(12) United States Patent
Tannenbaum et al.

(10) Patent No.: US 6,248,103 B1
(45) Date of Patent: Jun. 19, 2001

(54) APPARATUS AND METHOD FOR DYNAMIC COOLING OF BIOLOGICAL TISSUES FOR THERMAL MEDIATED SURGERY USING LONG LASER PULSES

(75) Inventors: Sam Tannenbaum, Claremont; Stuart Nelson, Laguna Niguel, both of CA (US); Thomas Milner, Austin; Bahman Anvari, Houston, both of TX (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/322,311

(22) Filed: May 28, 1999

Related U.S. Application Data

(63) Continuation-in-part of application No. 08/870,467, filed on Jun. 6, 1997, now Pat. No. 5,979,454, which is a continuation-in-part of application No. 08/963,531, filed on Nov. 3, 1997, now abandoned, which is a continuation-in-part of application No. 08/441,930, filed on May 15, 1995, now Pat. No. 5,814,040, which is a continuation of application No. 08/222,976, filed on Apr. 5, 1994, now abandoned.

(51) Int. Cl.[7] .................................................. A61B 18/18
(52) U.S. Cl. .............................................. 606/9; 128/898
(58) Field of Search ................................ 606/2, 3, 9–12, 606/20–24; 607/89; 128/898

(56) References Cited

U.S. PATENT DOCUMENTS

| 5,057,104 | 10/1991 | Chess . | |
|---|---|---|---|
| 5,344,418 | 9/1994 | Ghaffari . | |
| 5,810,801 | 9/1998 | Anderson et al. . | |
| 5,814,040 | * 9/1998 | Nelson et al. | 606/9 |
| 5,820,626 | 10/1998 | Baumgardner . | |
| 5,979,454 | * 11/1999 | Anvari et al. | 128/898 |

OTHER PUBLICATIONS

Nelson, et al. (1995) "Dynamic Epidermal Cooling During Pulsed Laser Treatment of Port–Wine Stain", Arch. Dermatol., vol. 131, pp. 695–700.

Anvari, et al., (1995) "Selective Cooling of Biological Tissues: Application for Thermally Mediated Therapeutic Procedures", Phys. Med. Biol., vol. 40, pp. 241–252.

* cited by examiner

*Primary Examiner*—Michael Peffley
(74) *Attorney, Agent, or Firm*—Daniel L. Dawes

(57) ABSTRACT

A method for performing laser treatment of biological tissues is performed by cooling a selected portion of the biological tissue for a predetermined first time period to establish a predetermined nonequilibrium dynamic temperature gradient through the tissue so that substantially only the selected portion of the biological tissue is cooled by a predetermined minimum temperature drop. The temperature gradient is established by providing a spurt of a predetermined amount of cryogenic liquid in direct contact with the biological tissue. A superficial and deeper part of the selected portion of the biological tissue is immediately irradiated for a time period which is approximately equal to or in excess of one millisecond. The irradiation is effective to thermally treat the deeper part of the biological tissue while leaving the superficial part of the biological tissue substantially undamaged. Heat is quickly dissipated from the superficial part of the biological tissue by means of supplying the latent heat of vaporization to the cryogenic liquid. The selected portion of the biological tissue is cooled for a predetermined third time period overlapping with the second time period by providing one or more additional spurts of predetermined corresponding amounts of cryogenic liquid in direct contact with the biological tissue at the site which is being irradiated in order to maintain the selected portion of the biological tissue at or below an average selected temperature.

20 Claims, 3 Drawing Sheets

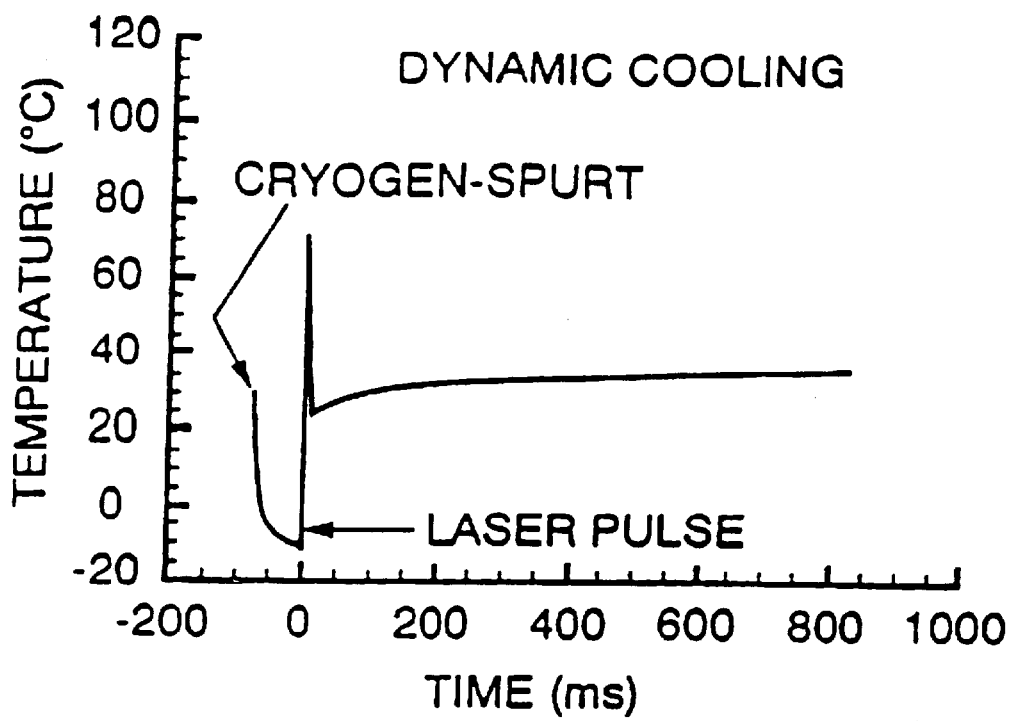
FIG. 4
FIG. 5
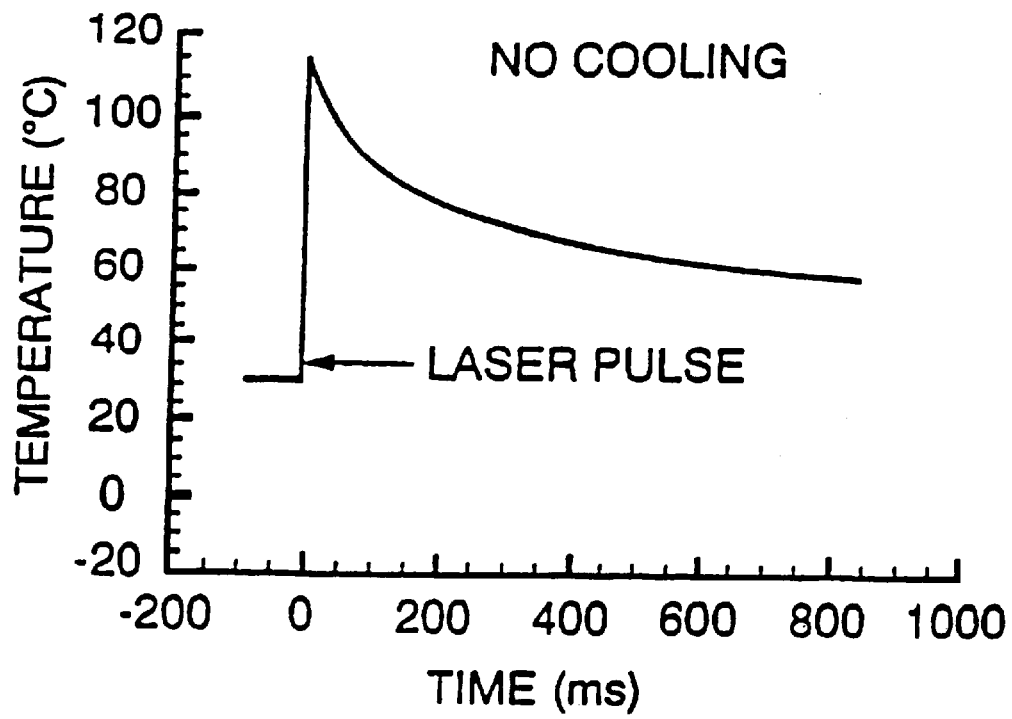

APPARATUS AND METHOD FOR DYNAMIC COOLING OF BIOLOGICAL TISSUES FOR THERMAL MEDIATED SURGERY USING LONG LASER PULSES

RELATED APPLICATIONS

The present application is a continuation in part of application Ser. No. 08/870,467, filed Jun. 6, 1997, now issued as U.S. Pat. No. 5,979,454, and of application Ser. No. 08/963,531, filed Nov. 3, 1997 (now abandoned). Application Ser. No. 08/870,467, now issued as U.S. Pat. No. 5,979,454, is a continuation in part of application Ser. No. 08/441,930, filed May 15, 1995, now issued as U.S. Pat. No. 5,814,040, which in turn was a continuation of copending application Ser. No. 08/222,976, filed Apr. 5, 1994, which was abandoned. U.S. Pat. No. 5,814,040 and application Ser. No. 08/870,467, now issued as U.S. Pat. No. 5,979,454, are herein incorporated by reference as if set out in their entirety.

BACKGROUND OF THE INVENTION

1. Field of the Invention

The invention relates to the field of laser surgery, and in particular, to the thermal treatment of biological tissues with laser pulses of the order of 10 ms or longer.

2. Description of the Prior Art

The illustrated embodiment of the invention is described below in the context of treatment of port wine stain birthmarks in human skin, although the scope of the invention is much broader in that it applies to all types of thermal surgeries or mediations. Thus use on hair, tattoo, and wrinkle removal are included as some of the examples. A port wine stain is congenital, progressive, vascular malformation of the dermis involving capillaries and possibly perivenular nerves. Port wine stains occur in approximately three of one thousand live births. Although port wine stains may be found anywhere on the body, they mostly appear on the face and are noted over the dermatome distribution of the first and second trigeminal nerves.

In early childhood, port wine stains are faint pink macules, but the lesions tend to darken progressively to red-purple and by middle age, often become raised as a result of the development of vascular papules or nodules and occasionally tumors. The hypertrophy of underlying bone and soft tissue occurs in approximately two-thirds of the patients with port wine stain, and serves to further disfigure the facial features of many children.

The prior art treatments for port wine stain includes scalpel surgery, ionizing radiation, skin grafting, dermabrasion, cryosurgery, tattooing and electrotherapy. Clinical results have been considered unsatisfactory due to the cosmetically unacceptable scarring post treatment. All of these prior art techniques are no longer considered viable treatment options for this reason.

A flashlamp-pumped pulsed dye laser offers a superior approach and therapy due to its ability to selectively destroy cutaneous blood vessels. Light passing through the epidermis is preferentially absorbed by hemoglobin which is the major chromophore in blood in the ectatic capillaries in the upper dermis. The radiant energy is converted to heat causing thermal damage and thrombosis in the targeted vessels. Prior art studies have shown that the flashlamp-pumped pulsed dye laser produce good results in the many pediatric and adult patients.

Histopathological studies of port wine stains show a normal epidermis overlying an abnormal plexus of dilated blood vessels located on a layer in the upper dermis as diagrammatically depicted in cross sectional view in FIG. 1. The predominate endogenous cutaneous chromophores, absorbing light at the 585 nanometer wavelength produced by flashlamp-pumped pulsed dye laser, are melanin and hemoglobin. Therefore, the overlying epidermal pigment layer comprises a barrier or an optical shield through which the light must first pass to reach the underlying port wine stain blood vessels. The absorption of laser energy by melanin causes localized heating in the epidermis and reduces the light dosage reaching the blood vessels, thereby decreasing the amount of heat produced in the targeted port wine stains and leading to suboptimal blanching of the lesion.

The ratio of heat generated in port wine stains to that of the epidermis is a measure of the relative heating of the port wine stain relative to the epidermis. The best clinical results realized in a port wine stain patient undergoing laser therapy are obtained when the patient's ratio of heat generated in the port wine stain to that in the epidermis is greater than or equal to one. Unfortunately, for many lesions, the threshold for epidermal damage following laser therapy is very close to the threshold for permanent blanching of the port wine stain.

One prior art method which has been tried is the application of ice cubes to the skin surface prior to laser treatment, B. A. Gilchrest et al., *"Chilling Port Wine Stains Improves the Response to Argon Laser Therapy,"* Plast. Reconstr. Surg. 1982; 69:278–83. However, these treatments have not proven entirely satisfactory, nor more importantly led to an improved therapeutic response, that is improved blanching of the port wine stain.

Other prior art attempts to provide surface cooling of the epidermis using plastic bags filled with ice placed on the skin surface for five minutes, compressed freon gas used during irradiation, or chilled water spread directly on the area being irradiated have also been explored, A. J. Welch et al., *"Evaluation of Cooling Techniques for the Protection of the Epidermis During ND-YAG Laser Irradiation of the Skin,"* Neodymium-YAG Laser in Medicine, Stephen N. Joffe editor 1983. However, these studies were done with pig cadaver tissue and normally utilized cooling periods of 2 to 14 seconds. The reported results with freon were good in only 28.5 percent of the cases, in some cases, the skin surface was momentarily frozen, and in others, the freon jet was found to overcool the skin surface.

Therefore, what is needed is some type of methodology or apparatus which can be effectively used to uniformly provide positive results, namely allowing treatment of deeper or selected layers of tissue without nonspecific damage to the upper or nonselected layers using longer pulses effective for treatment of larger port wine stains and other larger chromophore depositions.

BRIEF SUMMARY OF THE INVENTION

Larger dermal tissue structures require larger amounts of laser energy to be effectively treated. Because of thermal diffusion, when longer laser pulses are applied to dermal tissue structures, some of this added thermal energy will still be deposited in the epidermis during the laser pulse, and additional heat will diffuse into the epidermis from the heated dermal tissue structures after the laser pulse. These two effects could potentially raise the temperature in the epidermis to higher values than in current treatments. For this reason, cryogen spray cooling to protect the epidermis during laser treatment with long pulse lengths and higher laser doses will need to modified from the protocol provided for shorter laser pulses.

Hence, multiple cryogen spurts are applied immediately before, during and after a single 10–100 ms laser pulse. The cryogen spurts are similar in amount and duration to those used in shorter laser pulse treatments, but their repetition is effective in reducing and in most cases eliminating the damage to the epidermis during laser treatment of dermal tissue structures. The repetition rate is adjusted not only to protect the epidermis from the longer direct laser exposure of the epidermis, but to accommodate thermal diffusion from the dermis also due to the longer direct laser exposure of the dermis.

More specifically, the invention is a method for performing laser treatment of biological tissues comprising the steps of cooling a selected portion of the biological tissue for a predetermined first time period to establish a predetermined nonequilibrium dynamic temperature gradient through the tissue so that substantially only the selected portion of the biological tissue is cooled by a predetermined minimum temperature drop. The predetermined dynamic temperature gradient is established by providing a spurt of a predetermined amount of cryogenic liquid in direct contact with the biological tissue for the first time period at a site which is later irradiated for a predetermined second time period. A superficial and deeper part of the selected portion of the biological tissue is immediately irradiated after the first time period for the second time period which is approximately equal to or in excess of one millisecond. The irradiation is effective to thermally treat the deeper part of the biological tissue while leaving the superficial part of the biological tissue substantially undamaged. The cryogenic liquid has a latent heat of vaporization. The superficial part of the biological tissue is cooled for the second time period by a change of state of the cryogenic liquid to vapor. Heat is quickly dissipated from the superficial part of the biological tissue by means of supplying the latent heat of vaporization to the cryogenic liquid. The heat is dissipated in an amount as determined by the predetermined amount of cryogenic liquid applied to the superficial part of the biological tissue. The amount of dissipation of the heat from the superficial part of the biological tissue is specified by the predetermined amount of the cryogenic liquid applied to the superficial part of the biological tissue and by the latent heat of vaporization of the cryogenic liquid.

The selected portion of the biological tissue is cooled for a predetermined third time period overlapping with the second time period by providing one or more additional spurts of predetermined corresponding amounts of cryogenic liquid in direct contact with the biological tissue at the site which is being irradiated in order to maintain the selected portion of the biological tissue at or below an average selected temperature.

The superficial part is adjacent to the deeper part and the step of irradiating the deeper part comprises the step of irradiating the deeper part of the biological tissue through the superficial part. In the illustrated embodiment, the biological tissue is skin. The superficial part is epidermis and the deeper part is dermis lying beneath melanin contained in the epidermis. The step of establishing a predetermined dynamic temperature profile establishes a dynamically cooled profile substantially only in the epidermis.

The cooling with the cryogenic spurt is performed by disposing cryogenic in the form of droplets or as a cryogenic mist at the site. The method can also be thought of as establishing a thermal heat sink thermally coupled to the superficial part of the biological tissue. The establishment of the thermal heat sink comprises the step of substantially eliminating an air-to-surface insulating barrier at the superficial part of the biological tissue.

In the illustrated embodiment cooling is performed with the cryogenic spurt being applied to the superficial part of the biological tissue, namely disposing a liquid at a predetermined cooled temperature onto the surface of the superficial part of the biological tissue. The liquid has a boiling point below the normal temperatures of the superficial part of the biological tissue. The first predetermined time period of the cryogenic spurt has a time duration sufficient to provide approximately a 40–50 degree Centigrade temperature drop at the surface of the superficial part of the biological tissue. The duration of each of the cryogenic spurts is of the order of tens of milliseconds.

The method further comprises the step of reestablishing a predetermined dynamic temperature profile in the superficial part of the biological tissue after irradiation of the deeper part of the biological tissue. The step of reestablishing the predetermined dynamic temperature profile in the superficial part of the biological tissue is performed after both the superficial and deeper parts of the biological tissue are irradiated. The reestablishment is achieved by applying additional cryogen spurts to the superficial part after or during laser irradiation thereof. Each of the spurts, however, as similar in duration or amount to the cooling protocol performed with substantial shorter laser pulses, i.e. less than one millisecond in duration.

The invention is also defined as a method of laser treating tissue structures in human skin having an epidermis containing melanin and a dermis containing the targeted tissue structures. The method comprises dynamically cooling the epidermis by directly applying a controlled amount of a cryogenic liquid to the epidermis such that onset of a predetermined nonequilibrium temperature profile within the epidermis is achieved within a first time period which is substantially shorter than the thermal diffusion time between the target site in the dermis and the overlying epidermis. Immediately thereafter the target site in the dermis is irradiated through the epidermis for a second predetermined time period approximately equal to or in excess of one millisecond, but being sufficient in length to selectively thermally mediate the target site for a time duration in which thermal diffusion between the epidermis and dermis may occur. The epidermis rapidly cooled by vaporizing the cryogenic liquid simultaneously with the step of irradiating. The amount of the cryogenic liquid is repeatedly applied in controlled amounts to the epidermis. The amount and its repetition of application are controlled by offsetting a rate of cooling of the epidermis by vaporization of the cryogenic liquid against a rate of heating of the epidermis by irradiation of the epidermis and thermal diffusion from the target site in the dermis to the epidermis.

The invention is still further defined as a method for performing laser treatment of biological tissues comprising cooling a first part of the biological tissue for a predetermined first time period by direct contact of a liquid cryogen to the first part to establish a predetermined nonequilibrium dynamic temperature gradient through the tissue, so that substantially only the first part of the biological tissue is cooled by a predetermined minimum temperature drop. The predetermined dynamic temperature gradient is defined in the biological tissue for the first time period at a site, which is later irradiated for a predetermined second time period. The first part and a second part of the biological tissue is irradiated for the second time period by the laser immediately after the first time period to thermally treat the second part of the biological tissue while leaving the first part of the biological tissue substantially undamaged. The first part of the biological tissue is cooled for the second time period simultaneously with irradiating by quickly dissipating heat from the first part of the biological tissue through a thin layer of the liquid cryogen on the first part of the biological tissue at a rate high enough to prevent thermal-induced biological damage to the first part of the biological tissue. The cooling is quickly terminated to prevent any substantial removal of heat from the second part of the biological tissue which would interfere with a thermal biological effect to the second part of the biological tissue. The cooling of the first part of the biological tissue simultaneously with the step of irradiating and the quick termination of the cooling is repeated by additional applications of direct contact of a liquid cryogen to the first part: (1) to prevent thermal damage to the first part during an extended pulse irradiation of one millisecond or greater by the laser; and (2) to accommodate thermal diffusion from the second part to the first part.

Still further the invention can be defined as a method for performing laser treatment of biological tissues comprising applying a first selected amount of cooling cryogenic liquid in direct contact with a selected proximate portion of the biological tissue for a selected first time period. The proximate portion and targeted chromophores in a selected adjacent and distal portion of the biological tissue are irradiated by a laser beam beginning from the end of the selected first time period and continuing through a selected second time period. The end of the selected first time period is controllable within a few milliseconds. The first time period is less than that required to substantially cool the targeted chromophores. The irradiation of the proximate and distal portion of the biological tissue at the end of the selected second time period is terminated. The end of the selected second time period is controllable within a few milliseconds. The second time period is less than that at which damage begins to occur in the proximate portion. A second selected amount of cooling cryogenic liquid is reapplied in direct contact with the selected proximate portion of the biological tissue for a selected third time period. Heat diffusion from the distal portion of the biological tissue, which is thermally mediated, is absorbed by the second selected amount of cooling cryogenic liquid so that damage to the proximate portion is substantially avoided notwithstanding the heat diffusion from the distal portion of the biological tissue and continued irradiation by the laser.

The invention and its various embodiments may be better visualized by now turning to the following drawings wherein like elements are referenced by like numerals.

BRIEF DESCRIPTION OF THE DRAWINGS

FIG. 4 is a graph of the skin surface temperature measurements obtained using a fast infrared detector focused on a port wine stain on a human patient who has had the site dynamically cooled immediately prior to the laser pulse.

FIG. 5 is a graph of the skin surface temperature measurements obtained as in the case of FIG. 4 from a test site on the same patient in which the test site has had no cooling.

Figure 1:
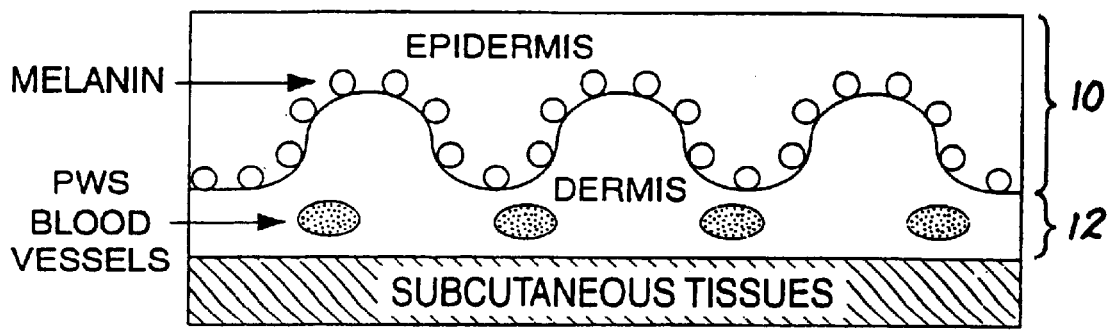
FIG. 1 is a highly diagrammatic side cross sectional view (not to scale) of human skin tissue having a port wine stain embedded in the dermis.

The invention and its various embodiments can now be understood in terms of the following detailed description.

DETAILED DESCRIPTION OF THE PREFERRED EMBODIMENTS

Dynamically cooling a target site in the epidermis of a patient undergoing laser therapy permits maximization of the thermal damage to the target site while at the same time minimizing nonspecific injury to the normal overlying epidermis. One or more cryogenic spurts are applied to the skin surface for a predetermined period of time, usually each spurt of the order of tens of milliseconds in duration so that the cooling remains localized in epidermis while leaving the temperature of deeper target site substantially unchanged. The result is that epidermal denaturation and necrosis which normally occurs in uncooled laser irradiated skin sites does not occur and that clinically significant thermal mediation of the target sites establishes that selective laser photothermolysis or mediation of the target site is achieved. In addition, dynamic epidermal cooling reduces patient discomfort normally associated with flashlamp-pumped pulsed dye laser therapy.

It is believed that all previously tried methods for cooling laser irradiated sites to prevent epidermal damage have essentially failed due to the thermal response of skin to prolonged cooling in which a near steady state temperature distribution is achieved. In steady state or prolonged cooling, the internal temperature increases linearly from the skin surface down into the subcutaneous layers. Therefore, in addition to cooling the epidermis, prolonged cooling also reduces the ambient temperature of the lower lying target site. Any increase in the threshold for epidermal damage achieved by temperature reduction is almost entirely offset by the additional energy required to heat the target site to a sufficient temperature to obtain selective laser photothermolysis or mediation.

With the application of dynamic cooling according to the invention, the epidermis can be selectively cooled. When a spurt of cryogen is applied to the skin surface for an appropriately short period, that is on the order of tens of milliseconds, the cooling remains localized in the epidermis while leaving the temperature of deeper target site unchanged. See, for example, FIG. 2, which is a graph of the dynamic cooling temperature profiles in skin as a function of depth for 10 to 100 microsecond cryogenic spurts. The vertical scale is shown in degrees Centigrade, while the horizontal scale is the depth in the tissue in millimeters.

Region 10 generally represents the position of the epidermal melanin. Region 12 diagrammatically depicts the typical depth at which target sites are found. Curve 14 is the temperature profile immediately after a 10 millisecond cryogenic spurt applied to the test site as described below. Curves 16, 18, 20 and 21 are the temperature profiles for 20, 30, 50 and 100 millisecond cryogenic spurts, respectively. It can be appreciated that for cryogenic spurts of these durations substantially all of the temperature cooling which occurs is in the area of the skin above target site region 12. Meanwhile temperatures in target site region 12 are unchanged.

If the skin is dynamically cooled so that heat is removed at a constant rate, a heat flux $F_0$, the instantaneous skin temperature, $T_S$, is given by the equation $$T_S(z, t) = T_i - \frac{F_0}{K}\left(2\sqrt{\frac{Xt}{\pi}}\, e^{z^2/4Xt} - z\,\text{erfc}\,\frac{z}{2\sqrt{Xt}}\right) \quad (1)$$

Where z is the skin depth, t is time, $T_i$ is the initial temperature at the skin surface, K is the thermal conductivity, X is the thermal diffusivity and erfc is the complementary error function. From equation (1), the temperature reduction of the skin surface in response to dynamic cooling can be shown to be:

$$\Delta T_0 = T_i - T_s(z=0, t_c) = \frac{2F_0}{K}(Xt_c/\pi)^{1/2} \quad (2)$$

Hence, surface temperature reduction is proportional to the heat flux, $F_0$, and the square root of the cooling time, $t_c$. For a given flux, the exposure time to the cryogenic spurt, $t_C$, must be long enough to produce a larger $\Delta T_0$, but short enough to avoid conductive cooling of the target site vessels in region 12.

Figure 3:
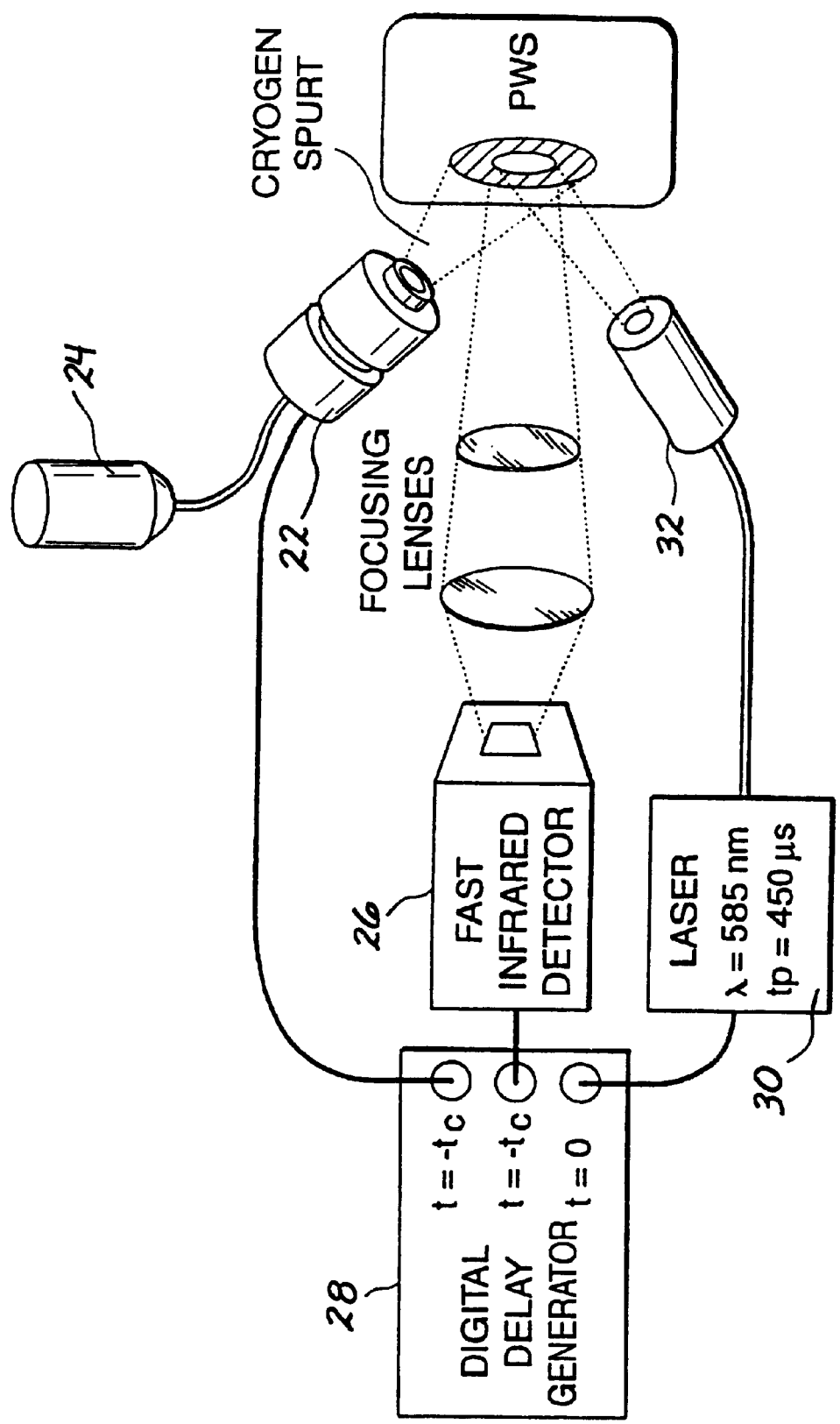
FIG. 3 is a simplified diagram showing use of the apparatus of the invention to conduct the methodology of the invention.

FIG. 3 is a highly diagrammatic depiction of one embodiment of the apparatus of the invention in which the methodology described above is practiced. A test cryogen, which in the illustrated embodiment is tetrafluoroethane, $C_2H_2F_4$ with a boiling point of −26.5 degrees Centigrade, and which is an environmentally compatible, nontoxic, nonflammable freon substitute, is used as a surface cooling agent. Multiple short cryogenic spurts, each having a duration of the order of tens of milliseconds are delivered onto the skin surface through an electronically controlled solenoid valve 22, which valve is supplied with test cryogen from a cryogenic reservoir 24.

A fast infrared detector 26, which in the illustrated embodiment is an InSb 128×128 focal plane array detector, sensitive in the 3–5 micron spectral range, is used to measure the skin surface temperature before, during and after the cryogenic spurt and laser pulse. Detector 26 is used in the system of FIG. 3 as a means of verifying test results. It is to be understood that in a commercial embodiment of the invention, detector 26 may be omitted or a simpler and less expensive thermal detector used in its place.

Detector 26 is triggered by a digital delay circuit 28 as manufactured by Stanford Research Systems of Sunnyvale, California. Solenoid valve 22 is similarly triggered at a time of $-t_C$ simultaneously with detector 26. At a time t=0, a flashlamp-pumped pulsed dye laser 30 operating at a wavelength of 585 nanometers with a pulse width of 450 microseconds is triggered.

The exposure time to the cryogenic spurt and the interval between the application of cryogenic spurts and the onset of the laser pulse are controlled by delay generator 28 and are usually less than 1 millisecond. The cryogenic spurt released from solenoid valve 22 is comprised of droplets of cryogen cooled by evaporation and mist formed by adiabatic expansion of vapor.

Droplets of cryogen have been found to provide a better heat sink that merely cooled gas. At the test site of the skin surface, the cryogenic spurt is made to cover an approximate circular zone of about 7 millimeters in diameter concentric with the laser spot which is approximately 5 millimeters in diameter. Clearly, the shape, size and disposition of the cooled region relative to the irradiated region can be varied according to the application in many ways consistent with the teachings of the invention.

Typically, target site patients undergoing laser therapy with a flashlamp-pumped pulse dye laser report sensations like a "hot pin prick" or a "elastic band snapping against the skin." The discomfort level is energy dependent and increases with high light dosages and also varies with the sensitivity of the treated anatomical site. Pain tolerance generally decreases with decreasing patient age. An additional advantage of dynamic epidermal cooling is reduction and in some cases, elimination of this discomfort. When the epidermis is rapidly cooled with cryogenic spurts longer than 20 milliseconds immediately prior to the laser exposure, the subjects in the present study reported feeling "nothing at all." Subjects treated with a cryogenic spurt as short as 5 milliseconds report significant improvement to the level of comfort associated with flashlamp-pumped pulsed dye laser therapy.

There are two reasons suggested for pain reduction reported by target site patients when using dynamic epidermal cooling prior to laser exposure. First, the maximum surface temperature achieved immediately after laser exposure is lower and in some cases as much as 40 degrees Centigrade lower on the cooled site as compared to the uncooled site. Second, cryogen remaining on the skin evaporates and continues to remove trapped heat through the skin-air interface following laser irradiation. Therefore, the temperature of the post irradiated epidermis decreases more rapidly on the cooled site as compared to the uncooled site.

Similar surface temperature reductions have been attained using shorter cryogen spurts. This suggests that the instantaneous temperature drop, To, prior to laser exposure is not the only thermal effect responsible for the observed results. Even more important is the rapid removal of heat from the epidermis after pulsed laser exposure due to the establishment of a large temperature gradient near the skin surface.

The heat loss from human skin in contact with air is insignificant because the tissue-air interface is an excellent thermal insulator. With no cooling, heat diffusing away from the absorbing melanin layer and target site builds up near the skin surface and produces an elevated surface temperature that persists for quite some time after laser exposure. Eventually, lateral thermal diffusion and cooling by blood perfusion eliminates the heat built up near the surface, but this may take several seconds.

Figure 2:
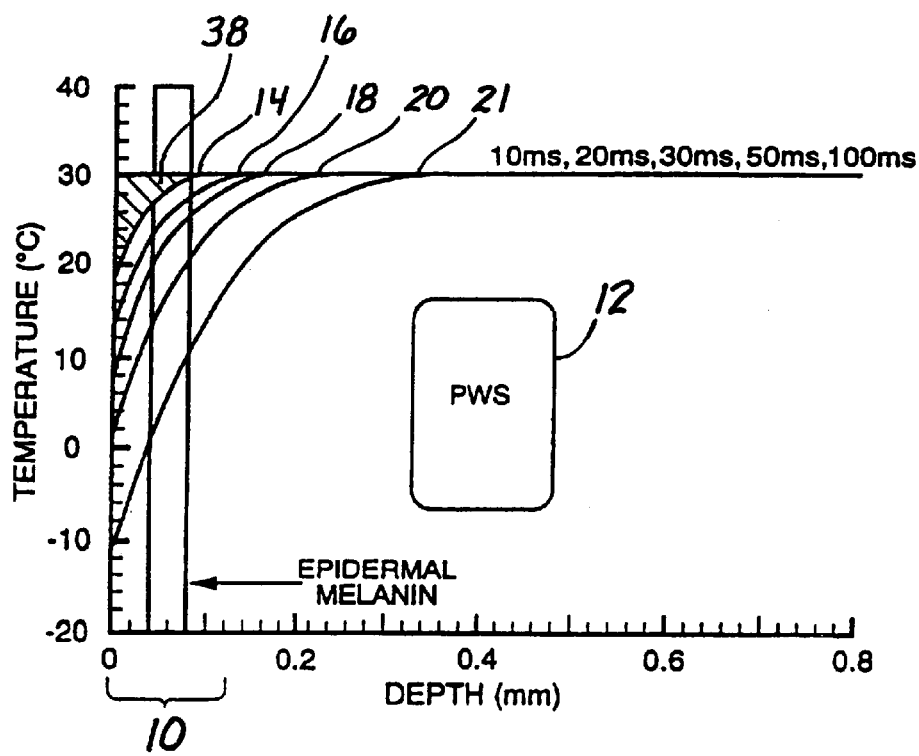
FIG. 2 is a graph of the dynamic cooling temperature profiles in skin as a function of depth for 10 to 100 microsecond cryogenic spurts.

It is believed that an important element in dynamic cooling is removal of heat that builds up near the skin surface by the evaporating cryogenic liquid. Cryogen applied to the skin creates a heat sink below the surface of the skin that can remove heat before, during and after laser exposure. The heat sink persists for as long as the liquid cryogen remains on the skin surface. For any given cryogenic spurt, the size or capacity of the sink is proportional to the area between the corresponding temperature curve shown in FIG. 2 and a horizontal line at ambient skin temperature with approximately 30 degrees Centigrade. This is represented in FIG. 2 as a striped area 38 for a 10 millisecond cryogenic spurt.

One goal then is to create with dynamic cooling a heat sink that can rapidly remove the trapped heat without cooling the target site in region 12. An important factor in drawing heat out of the skin is the temperature gradient that is established near the skin surface. The steeper the gradient, the faster a given quantity of heat is withdrawn. Thus, to be successful, the cryogen should produce a large surface temperature drop as quickly as possible. Moreover, the quantity of cryogen delivered can be controlled and thus, residual heat is removed by cryogen that has remained on the skin surface after laser exposure. If additional heat must be removed, more cryogen can be applied immediately after laser exposure. Thus, the present invention contemplates not only a cryogenic spurt immediately prior to laser exposure, but also one or more cryogenic spurts thereafter.

The complexity of the dynamic cooling process warrants a careful choice of the cryogen and optimization of several cooling parameters. According to the invention, the cryogen is selected based upon the following factors. The cryogen must have: (1) sufficient adhesion to maintain good surface contact with the skin; (2) a high thermal conductivity so the epidermis can be cooled very rapidly prior to laser exposure; (3) a low boiling point to establish a large temperature gradient at the surface; (4) a high latent heat of vaporization to sustain evaporative cooling of the epidermis after laser exposure; and (5) no adverse health or environmental effects. Although the illustrated embodiment has described the use of tetrafluoroethane, many other cryogens could be substituted with similar results provided that they had one or more of the above factors in their favor.

Further, according to the invention, selectivity of the dynamic cooling of the epidermis can be optimized by controlling: (1) duration of the cooling spurt or spurts; (2) quantity of cryogen deposited on the skin surface so that the effect of evaporative cooling can be maximized; (3) timing of dynamic cooling relative to laser exposure; and (4) the length of the laser pulse.

Further, it is contemplated that application can be maximized using a portable hand piece which incorporates a laser fiber together with a miniature solenoid valve to time release cryogenic spurts onto the skin. In this case, single hand-held unit would be employed replacing solenoid valve 22 and laser delivery hand piece 32 of FIG. 4. The use of a single instrument to provide both directed cryogenic sprays to selectively cool certain areas of the skin relative to the irradiated spot and to provide the laser beam is expressly contemplated.

The importance of dynamic epidermal cooling has broad implications for the development of future laser systems for target site therapy. Currently, only a small proportion of port wine stain patients are able to realize complete fading of their lesions even after undergoing multiple laser treatments. One reason for treatment failure has been the inadequate heat generation within large target site blood vessels. A 450 microsecond pulse duration shown in the illustrated embodiment is too short to generate sufficiently high core temperatures over long enough periods of time to destroy irreversibly large target site blood vessels. An improved therapeutic outcome is expected for laser systems utilizing the present invention with pulse durations of the order of several milliseconds. Although longer pulse durations will certainly destroy larger target site blood vessels, such laser systems will also produce greater epidermal injury due to nonspecific absorption by melanin and heat dissipation from the injured vessels. Thus, it is within the scope of the invention to selectively cool and protect the overlying epidermis during longer pulse exposures.

For example, in addition to repetitive patterns of pulsed cryogenic spurts on the laser site, the present invention contemplates the continuous gaseous flushing of the laser site before, during and after the laser exposure. The protocol by which the cooling substance is applied to create the heat sink on the epidermis surface is not limited or restricted in the invention as long as the time between the onset of when the cooling of the epidermis occurs and the laser firing is short when compared to the thermal diffusion time of the biological target sought to be thermally destroyed, or in this case, the target site.

Dynamic cooling as previously disclosed in connection with FIGS. 4 and 5 is directed to very short laser pulses (<1 ms) and the parent application from which this application is a continuation in part is directed to very long or continuous laser pulses. Thus, cryogen spray cooling has thus previously been illustrated as being used in conjunction with 10 ms laser heating pulses, but cryogen spray cooling can be used in conjunction with even longer laser pulses for the treatment, for example, of very large diameter blood vessels and other applications in which the input energy needed for effective thermal mediation is increased over the illustrated embodiments previously described.

The analytical solution for the temperature profile in the epidermis produced by heating melanin with laser pulses will serve to further illustrate the invention. For pulses longer than 1 ms, the epidermal temperature jump is affected by diffusion of the thermal energy as it is being delivered to the melanin layer. As a result, the peak temperature jump in the melanin layer at the end of the pulse is lower than it would be for a shorter laser pulse delivering the same total light energy dosage. This effect can be seen most easily by examining the equation for the temperature increase $\Delta T_p$ in the center of the melanin layer at the end of the laser pulse, which is obtained by solving the thermal diffusion equation with a laser heat source producing Q watts/cm$^3$ throughout a melanin layer of thickness d for an exposure or irradiation time period of $\tau_L$, the duration of the laser pulse. The result is:

$$\Delta T_p(\tau_L)=(Q\tau_L/pC)[erf(d^*/2)+d^*ierfc(d^*/2) \quad (3)$$

Where p is the tissue density, C is its specific heat, erf(x) is the error function, ierfc(x) is the integral from x to infinity of the complementary error function, (1-erf(x)), and d* is related to the thickness d of the melanin layer by the equation $$d^*=d/2(D\tau_L)^{1/2} \quad (4)$$

where D is the thermal diffusion coefficient.

From Equation (4) we find that for a typical melanin layer with thickness d =70 $\mu$m, d* is very large (d*>>1 ) for $\tau_L$<1 ms. Hence, from Eq (3)

$$\Delta T_p(\tau_L)=(Q\tau_L/pC)=\Delta T_0$$

where $\Delta T_0$ is the standard temperature increase used for a "short" pulse when there is no thermal diffusion during the laser heating. However, as can be found from Eq (3), for $\tau_L$=10 ms, diffusion reduces the temperature jump, $\Delta T_p(\tau_L)$, to $\frac{2}{3}$ $\Delta T_0$; and for a 100 ms laser pulse almost all of the thermal energy diffuses away from the melanin layer as it is being heated, reducing $\Delta T_p(\tau_L)$ to 0.1 $\Delta T_0$.

However, longer laser pulse durations in 10 to 100 ms range are desirable for optimal heating of large diameter PWS blood vessels. The result shown in Eq (3) is a particular case of the general result that we have obtained for the temperature increase $\Delta T(z, t)$ obtained by solving the heat diffusion equation throughout a melanin layer that extends from z=0 to z=d, namely:

$$T(z,t)=(Qt/2pC)[erf(z^*)+2z^*ierfc|z^*|+erf(d^*-z^*)+2(d^*-z^*)ierfc|d^*-z^*|]$$

where $z^*=z/2(Dt)^{1/2}$, and all other terms are as defined above. This result leads to Eq (3) at the center of me melanin layer where z=d/2. Note that this result holds for all z, both inside and outside the melanin layer, but neglects any effects due to the skin surface, which is located at some negative value of z in this coordinate system. The skin surface effects are not important for our calculations unless the heating lasts long enough for heat to diffuse to the skin surface and then reflect back to the melanin layer.

To summarize, because of thermal diffusion, a fixed laser energy dose in joules/cm$^3$ delivered to the skin surface by a long laser pulse produces a smaller temperature jump in the melanin layer than a short pulse; hence the likelihood of damage to the epidermis is reduced. Moreover, for his same reason it is likely that when longer laser pulses are available, larger laser doses will be used to treat the PWS blood vessels. Some of this added thermal energy will still be deposited in the epidermis during the laser pulse, and additional heat will diffuse into the epidermis from the heated PWS blood vessels after the laser pulse. These two effects could potentially raise the temperature in the epidermis to higher values than in current treatments. For this reason, cryogen spray cooling will be even more desirable to protect the epidermis during, laser treatment of PWS blood vessels with long pulse lengths and higher laser doses, Since cryogen spurts with durations as short as a few milliseconds have been shown to provide significant cooling of the epidermis, we propose that multiple cryogen spurts before, during and after a lone 10–100 ms laser pulse will be effective in reducing and in most cases eliminating the damage to the epidermis during laser treatment of PWS blood vessels and other dermatoses. The same cryogen spurt delivery system used for use in conjunction with short pulse laser heating can also be used in conjunction with longer pulse laser heating.

Further, although the present invention has been described in the context of target sites, it must be specifically understood that the use of dynamic cooling in conjunction with laser surgery can also be directly applied to many different applications in the field of dermatology, such as laser treatment collagen and wrinkles, treatment of tattoos, and epidermal and dermal melanoses, or hair removal; in the field of ophthalmology, such as cornea surgery; orthopedics and in the field of dentistry. The methodology and apparatus can be applied in any case where it is important to maintain the temperature or thermal damage to adjacent or overlying tissues at a low level while heating or thermally impacting other target tissues.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for performing laser treatment of biological tissues comprising:

cooling a selected portion of said biological tissue for a predetermined first time period to establish a predetermined nonequilibrium dynamic temperature gradient through said tissue so that substantially only said selected portion of said biological tissue is cooled by a predetermined minimum temperature drop, said predetermined dynamic temperature gradient being established by providing a spurt of a predetermined amount of cryogenic liquid in direct contact with said biological tissue for said first time period at a site which is later irradiated for a predetermined second time period;

immediately after said first time period irradiating a superficial and deeper part of said selected portion of said biological tissue for said second time period approximately equal to or in excess of one millisecond to thermally treat said deeper part of said biological tissue while leaving said superficial part of said biological tissue substantially undamaged, said cryogenic liquid having a latent heat of vaporization, said superficial part of said biological tissue being cooled for said second time period by a change of state of said cryogenic liquid to vapor, heat being quickly dissipated from said superficial part of said biological tissue by means of supplying said latent heat of vaporization to said cryogenic liquid, said heat being dissipated in an amount as determined by said predetermined amount of cryogenic liquid applied to said superficial part of said biological tissue, the amount of dissipation of said heat from said superficial part of said biological tissue being specified by said predetermined amount of said cryogenic liquid applied to said superficial part of said biological tissue and by said latent heat of vaporization of said cryogenic liquid; and cooling said selected portion of said biological tissue for a predetermined third time period overlapping with said second time period by providing one or more additional spurts of predetermined corresponding amounts of cryogenic liquid in direct contact with said biological tissue at said site which is being irradiated to maintain said selected portion of said biological tissue at or below an average selected temperature, whereby said deeper part of said selected portion of said biological tissue may be laser treated without damage to said superficial part.

2. The method of claim 1 wherein said superficial part is adjacent to said deeper part and said step of irradiating said deeper part comprises the step of irradiating said deeper part of said biological tissue through said superficial part.

3. The method of claim 2 wherein said biological tissue is skin, said superficial part being epidermis and said deeper part being dermis lying beneath melanin contained in said epidermis and wherein said step of establishing a predetermined dynamic temperature profile establishes a dynamically cooled profile substantially only in said epidermis.

4. The method of claim 1 wherein cooling with said cryogenic spurt comprises disposing cryogenic droplets at said site.

5. The method of claim 1 wherein cooling with said cryogenic spurt comprises disposing a cryogenic mist at said site.

6. The method of claim 1 further comprising establishing a thermal heat sink thermally coupled to said superficial part of said biological tissue.

7. The method of claim 6 where establishing a thermal heat sink comprises the step of substantially eliminating an air-to-surface insulating barrier at said superficial part of said biological tissue.

8. The method of claim 1 wherein cooling with said cryogenic spurt applied to said superficial part of said biological tissue comprises disposing a liquid at a predetermined cooled temperature onto the surface of said superficial part of said biological tissue, said liquid having a boiling point below normal temperatures of said superficial part of said biological tissue and wherein said first predetermined time period of said cryogenic spurt has a time duration sufficient to provide approximately a 40–50 degree Centigrade temperature drop at said surface of said superficial part of said biological tissue.

9. The method of claim 8 wherein said duration of each of said cryogenic spurts is of the order of tens of milliseconds.

10. The method of claim 1 further comprising reestablishing a predetermined dynamic temperature profile in said superficial part of said biological tissue after irradiation of said deeper part of said biological tissue, said superficial and deeper parts of said biological tissue being thermally coupled.

11. The method of claim 10 wherein said step of reestablishing said predetermined dynamic temperature profile in said superficial part of said biological tissue is performed after both said superficial and deeper parts of said biological tissue are irradiated by applying additional cryogen to said superficial part after or during laser irradiation thereof, each of said spurts being similar in duration or amount of cryogen applied with laser pulses less than one millisecond in duration.

12. A method of laser treating tissue structures in human skin having an epidermis containing melanin and a dermis containing said tissue structures comprising:
dynamically cooling said epidermis by directly applying a controlled amount of a cryogenic liquid to said epidermis such that onset of a predetermined nonequilibrium temperature profile within said epidermis is achieved within a first time period which is substantially shorter than the thermal diffusion time between said target site in said dermis and said overlying epidermis; and
immediately thereafter irradiating said target site in said dermis through said epidermis for a second predetermined time period approximately equal to or in excess of one millisecond, but being sufficient in length to selectively thermally mediate said target site for a time duration in which thermal diffusion between said epidermis and dermis may occur;
simultaneously with said step of irradiating, rapidly cooling said epidermis by vaporizing said cryogenic liquid, said amount of said cryogenic liquid being repeatedly applied in controlled amounts of said cryogenic liquid to said epidermis, said amount and its repetition of application being controlled by offsetting a rate of cooling of said epidermis by vaporization of said cryogenic liquid against a rate of heating of said epidermis by said step of irradiating and thermal diffusion from said target site in said dermis to said epidermis;
whereby said target site is destroyed without substantial biological damage to said epidermis.

13. The method of claim 12 wherein said epidermis is dynamically cooled by subjecting said epidermis to a spurt of cryogen to establish a predetermined nonequilibrium temperature profile on said epidermis within said first predetermined time period.

14. The method of claim 13 wherein said first predetermined time period is of the order of tens of milliseconds.

15. The method of claim 14 wherein said predetermined nonequilibrium temperature profile has a skin surface temperature of at least approximately 40 degrees Centigrade below normal skin temperature at the end of said first predetermined time period.

16. A method for performing laser treatment of biological tissues comprising:
cooling a first part of said biological tissue for a predetermined first time period by direct contact of a liquid cryogen to said first part to establish a predetermined nonequilibrium dynamic temperature gradient through said tissues so that substantially only said first part of said biological tissue is cooled by a predetermined minimum temperature drop, said predetermined dynamic temperature gradient being defined in said biological tissue for said first time period at a site which is later irradiated for a predetermined second time period; and
immediately after said first time period, irradiating said first part and a second part of said biological tissue for said second time period by said laser to thermally treat said second part of said biological tissue while leaving said first part of said biological tissue substantially undamaged; and
simultaneously with irradiating, cooling said first part of said biological tissue for said second time period by quickly dissipating heat from said first part of said biological tissue through a thin layer of said liquid cryogen on said first part of said biological tissue at a rate high enough to prevent thermal-induced biological damage to said first part of said biological tissue; and
quickly terminating said cooling to prevent any substantial removal of heat from said second part of said biological tissue which would interfere with a thermal biological effect to said second part of said biological tissue; and
repeating the cooling of said first part of said biological tissue simultaneously with said step of irradiating and the quick termination of the cooling by additional applications of direct contact of a liquid cryogen to said first part to prevent thermal damage to said first part during an extended pulse irradiation of one millisecond or greater by said laser and to accommodate thermal diffusion from said second part to said first part,
whereby said second part of said selected portion of said biological tissue may be laser treated without damage to said first part.

17. A method for performing laser treatment of biological tissues comprising:

applying a first selected amount of cooling cryogenic liquid in direct contact with a selected proximate portion of said biological tissue for a selected first time period having a beginning and an end;

irradiating said proximate portion and targeted chromophores in a selected adjacent and distal portion of said biological tissue by a laser beam beginning from said end of said selected first time period and continuing through a selected second time period having a beginning and an end, said end of said selected first time period being controllable within a few milliseconds, and wherein said first time period is less than that required to substantially cool said targeted chromophores; and ending irradiation of said proximate and distal portion of said biological tissue at said end of said selected second time period, said end of said selected second time period being controllable within a few milliseconds, and wherein said second time period is less than that at which damage begins to occur in said proximate portion, reapplying a second selected amount of cooling cryogenic liquid in direct contact with said selected proximate portion of said biological tissue for a selected third time period having a beginning and an end; wherein heat diffusion from said distal portion of said biological tissue being thermally mediated is absorbed by said second selected amount of cooling cryogenic liquid so that damage to said proximate portion is substantially avoided notwithstanding said heat diffusion from said distal portion of said biological tissue and continued irradiation by said laser.

18. The method of claim 17 wherein said first and third time periods are selected according to thermal dosage provided to said proximate portion of said biological tissue during said second time period, which first and third time periods are adjusted according to individual patient characteristics affecting said thermal dosage to said proximate portion during said second time period, and wherein said second time period is selected to provide a thermal dosage to said targeted chromophores of said distal portion of said biological tissue, which thermal dosage is effective to surgically mediate said targeted chromophores.

19. The method of claim 17 wherein said cryogenic liquid is applied to said biological tissue in liquid form by fine droplet spraying.

20. The method of claim 17 wherein applying, irradiating, and ending irradiation are selectively repetitively performed according to patient characteristics with a repetition rate controllable within a few milliseconds.

* * * * *

UNITED STATES PATENT AND TRADEMARK OFFICE
CERTIFICATE OF CORRECTION

PATENT NO.   : 6,248,103 B1
DATED        : June 19, 2001
INVENTOR(S)  : Sam Tannenbaum, Stuart Nelson, Thomas Milner and Bahman Anvari It is certified that error appears in the above-identified patent and that said Letters Patent is hereby corrected as shown below:

Column 1,
Line 19, insert the following paragraph:
-- This invention was made with Government support under Grant No. RR06988, awarded by the National Institutes of Health. The Government has certain rights in this invention. --

Signed and Sealed this

Sixth Day of August, 2002

Attest:

Attesting Officer

JAMES E. ROGAN
Director of the United States Patent and Trademark Office